United States Patent [19]
Fischer

[11] Patent Number: 5,785,057
[45] Date of Patent: Jul. 28, 1998

[54] MEDICAL POSITIONING DEVICE

[76] Inventor: Sally A. Fischer, 598 Shenandoah, Clawson, Mich. 48017

[21] Appl. No.: 763,799

[22] Filed: Dec. 11, 1996

[51] Int. Cl.$^6$ ....................................... A61F 5/37
[52] U.S. Cl. ...................... 128/846; 128/878; 128/879
[58] Field of Search ................................ 128/845, 846, 128/877, 878, 879; 602/5, 20, 21, 22, 12, 62, 64, 65; 2/171; 5/607, 647

[56] References Cited

U.S. PATENT DOCUMENTS

| | | | |
|---|---|---|---|
| 2,679,842 | 6/1954 | Brill | 128/878 |
| 3,657,741 | 4/1972 | Blanco . | |
| 3,785,371 | 1/1974 | Lewis . | |
| 4,465,064 | 8/1984 | Boone | 602/12 |
| 4,476,857 | 10/1984 | Levine . | |
| 4,982,745 | 1/1991 | Shields | 128/877 |
| 5,027,799 | 7/1991 | Laico et al. . | |
| 5,291,903 | 3/1994 | Reeves . | |
| 5,307,521 | 5/1994 | Davis . | |
| 5,335,888 | 8/1994 | Thomsen . | |
| 5,344,406 | 9/1994 | Spooner . | |
| 5,362,306 | 11/1994 | McCarver et al. . | |
| 5,368,550 | 11/1994 | Sisley . | |
| 5,372,145 | 12/1994 | Berger . | |
| 5,376,066 | 12/1994 | Phillips et al. . | |
| 5,395,302 | 3/1995 | Botha et al. . | |
| 5,397,296 | 3/1995 | Sydor et al. . | |
| 5,405,312 | 4/1995 | Jacobs . | |
| 5,419,756 | 5/1995 | McConnell . | |
| 5,472,000 | 12/1995 | Olsen . | |
| 5,546,963 | 8/1996 | Doody | 128/878 |

*Primary Examiner*—Michael A. Brown
*Attorney, Agent, or Firm*—Young & Basile P.C.

[57] ABSTRACT

An apparatus for positioning an upper appendage portion of a body of a patient with respect to an operating room table having a mattress covering at least a portion of the operating room table and a leaf portion moveable out of a coplanar position with respect to a remaining portion of the operating room table during a surgical procedure. The apparatus includes an elongated rigid shell having a shallow curve or fossa for covering a lateral aspect of the arm of the patient and an end cap integrally formed to enclose one end of the shell for completely covering at least the hand and fingers of the patient. A sled is integrally formed as a portion of the shell for stabilizing the shell with respect to the operating room table. A base portion of the sled is spaced from the end cap a sufficient distance to allow insertion of the mattress covering the operating room table between the end cap and the base portion of the sled. The base portion of the sled is spaced longitudinally inward from an outer end of the end cap along the longitudinal length of the shell a sufficient distant to allow unimpeded movement of the leaf portion of the operating room table to and from a position coplanar with the remaining portion of the operating room table.

18 Claims, 4 Drawing Sheets

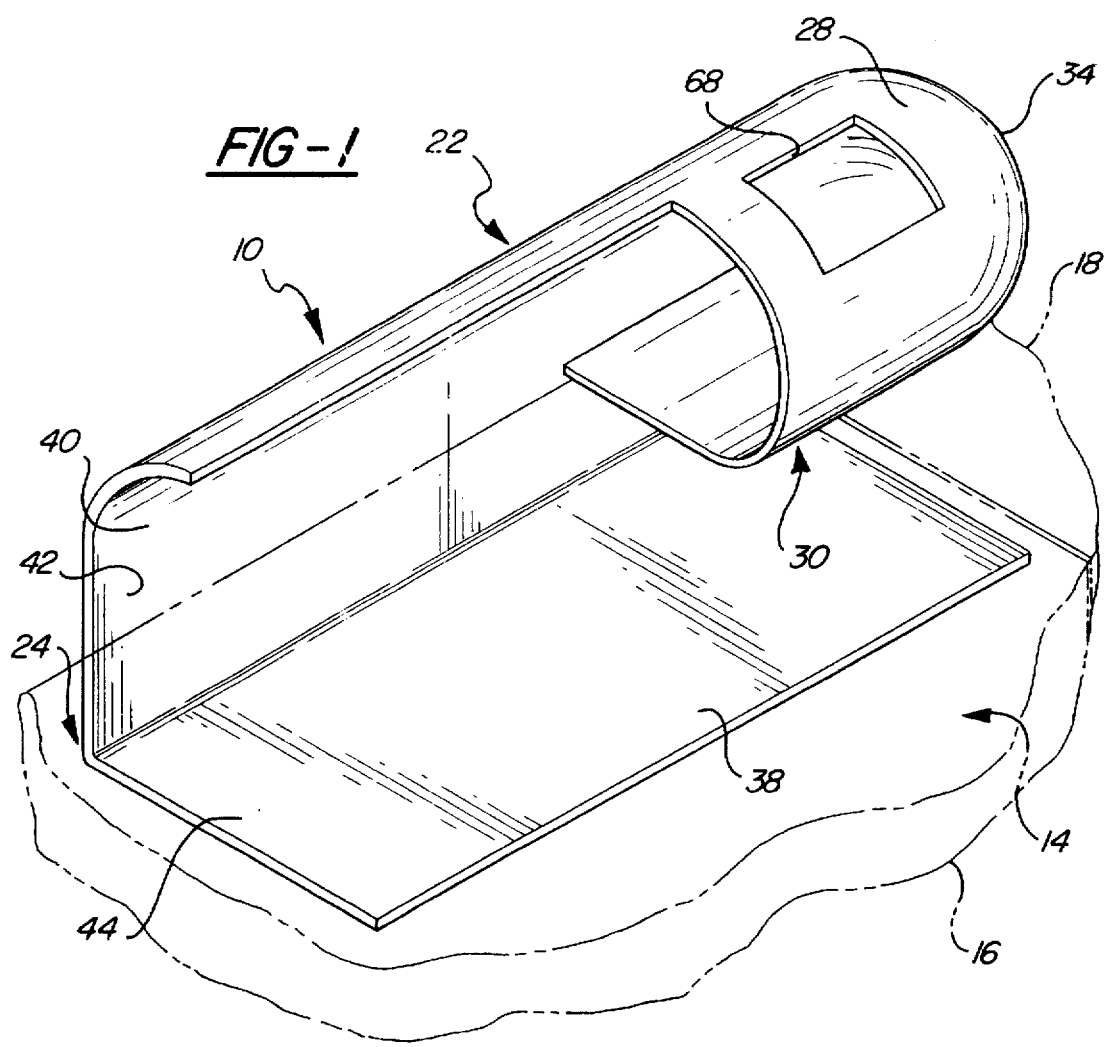
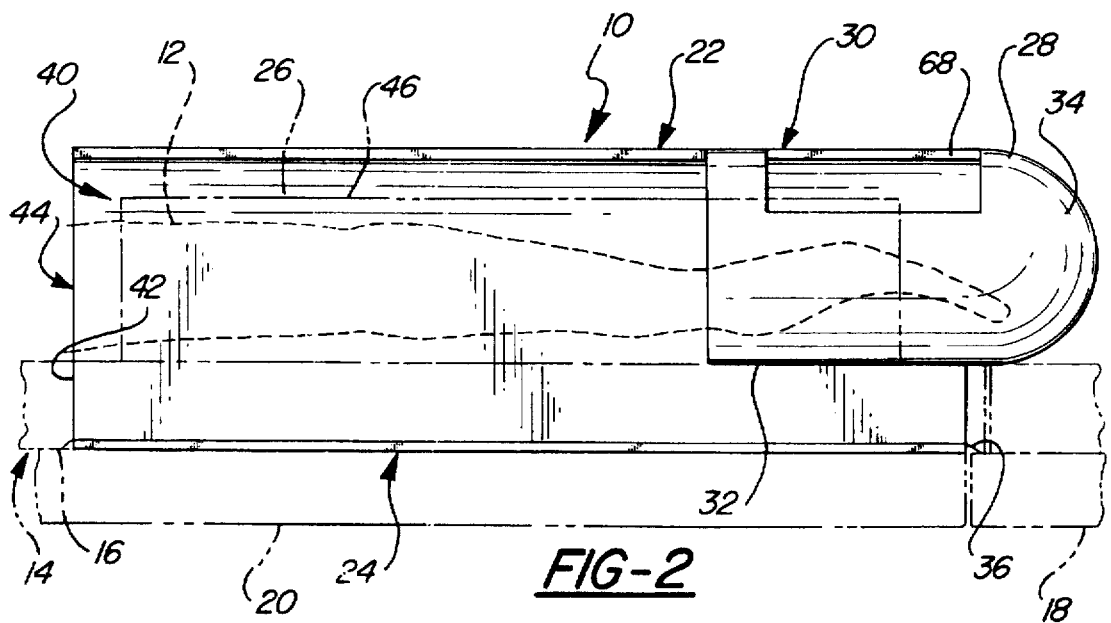

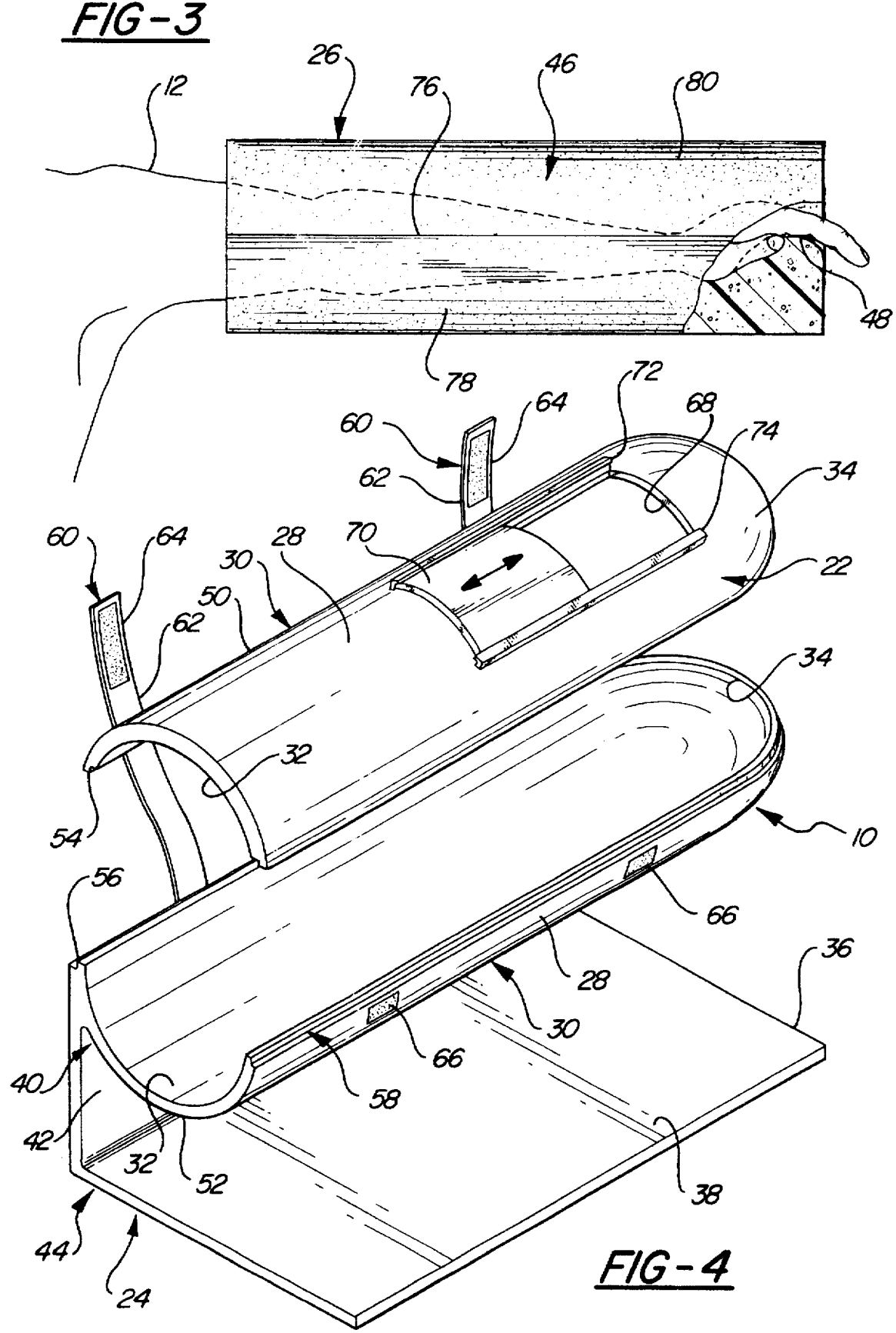

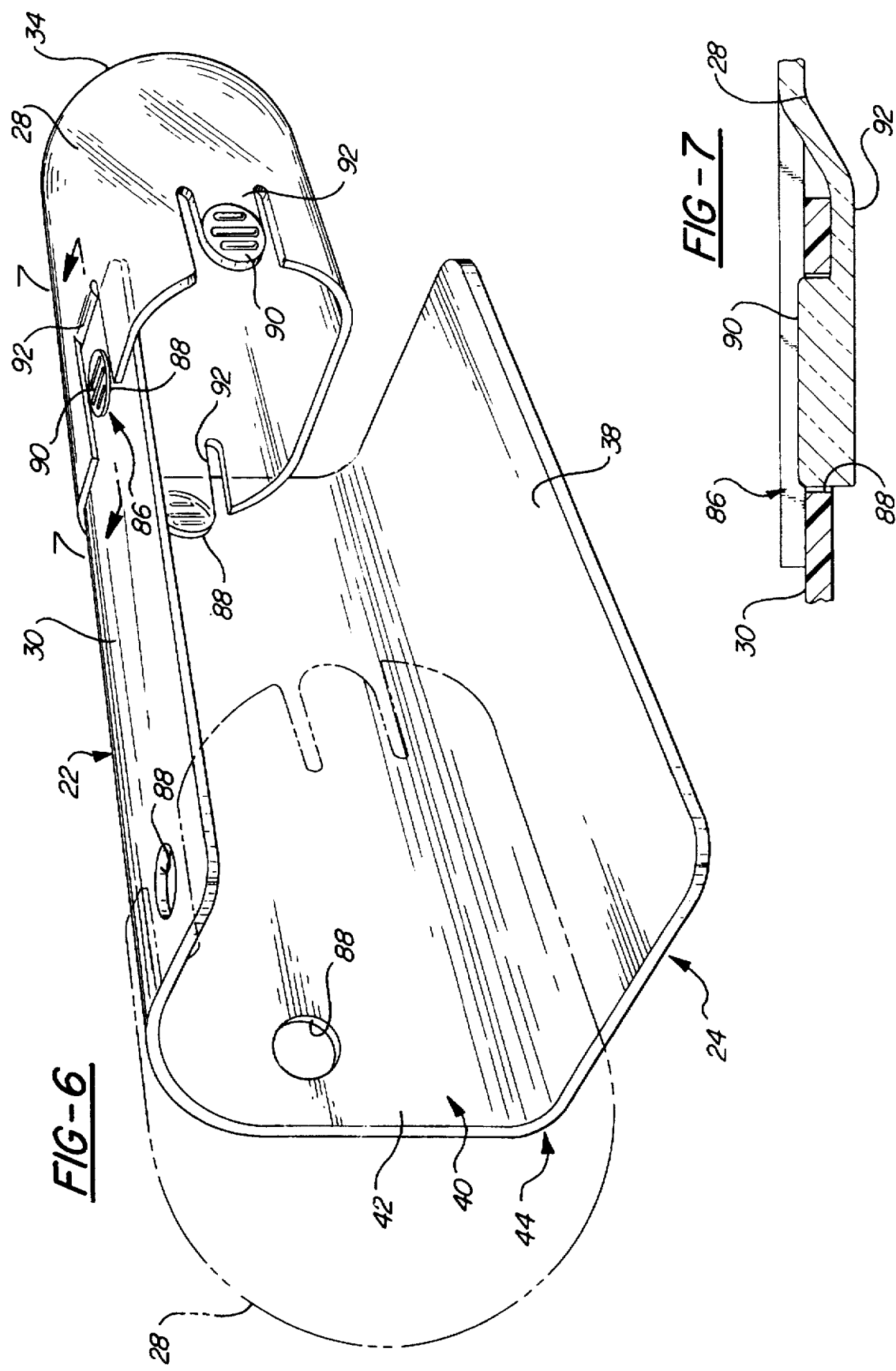

5,785,057

MEDICAL POSITIONING DEVICE

FIELD OF THE INVENTION

The present invention relates to a medical positioning device for positioning an upper appendage portion of a body of a patient with respect to a surgical table during a surgical procedure, and more particularly, to an apparatus for preventing injury to an upper appendage of a patient due to an object external to the body during a surgical procedure.

BACKGROUND OF THE INVENTION

During a medical operating room surgical procedure, it is important to position and protect a patient's ulnar nerve, hands and fingers from injury. Pressure on the ulnar nerve for an extended period of time during a surgical operation while the patient is anesthetized can cause damage to the nerve. The typical cause of pressure on the ulnar nerve is the edge of the operating table. In addition, when the surgical procedure employs the use of a hydraulic table, the patient's fingers can be subject to potential injury due to pinching between the moveable parts of the hydraulic table.

Currently, while preparing a patient for surgery of this type, the operating room nurse may protect the patient's fingers by wrapping the patient's hand supported by a relatively flat elongated member, such as an empty cardboard box of the appropriate size. The patient's arm and hands are then tucked and held in place by folding the surgical drape, or other covering, in the appropriate manner in order to cause the patient's own weight to maintain the tucked arms in the desired position extending along the length the patient's body. Typical surgeries that may require a patient's arms to be tucked could include, by way of example and not limitation, laparoscopy, open heart, thyroid, eye surgery, tonsils, carotid artery, or any other surgery involving the head and neck of the patient.

SUMMARY OF THE INVENTION

The present invention seeks to provide a medical positioning and protective device for use in an operating room to protect a patient's ulnar nerve, hands and fingers from injury during surgical operations. The hand and ulnar nerve protector according to the present invention supports the patient's arm and hand in a natural contour from the fingers to a point above the elbow. An apparatus according to the present invention positions a portion of a body of a patient during surgery and can include means for safeguarding an upper appendage of a patient from injury due to an object external to the body and means for anchoring the safeguarding means in a desired location during a surgical procedure.

A surgical operating room table, such as a hydraulic table, may include a leaf portion moveable out of a coplanar position with respect to a remaining portion of the surgical table, if required during a surgical procedure, such as in the case of a gynecological procedure. An apparatus according to the present invention can include an elongated rigid shell having a shallow curve for covering a lateral aspect of the arm of the patient and an enclosed end cap integrally formed at one end of the shell for completely covering the hand and fingers of the patient. A sled is integrally formed as a portion of the shell for stabilizing the shell with respect to the operating room table. A base portion of the sled is spaced from the end cap a sufficient distance to allow insertion of a mattress covering the operating room table between the end cap and the base portion of the sled. The base portion of the sled is spaced longitudinally inwardly from an outer end of the end cap along the longitudinal length of the shell a sufficient distance to allow unimpeded movement of the leaf portion of the operating room table.

The positioning device is designed to be used with an inner foam liner having approximately one inch thickness. The liner is open at both ends to allow the medical staff to reach in and pull the arm of a patient through the sleeve of the liner, if a patient is unable to position the liner over the arm. The liner sleeve may also be bifurcated, or rollable into a sleeve configuration from a planar form for easier placement over the arm of the patient. Preferably, the foam has a curved portion under the palm of the patient to support the natural contour of the hand. The padding extends passed the elbow to further protect the ulnar nerve area of the patient's arm.

The outer hard shell can be made of plastic, acrylic, or metal. The entire length of the shell is preferably approximately 24 inches. Preferably, the shell has a shallow curve or fossa designed to cover the lateral aspect of the arm and incorporates a shell cap at one end. The shell end cap is approximately 9 inches in length for completely covering the hand and fingers of the patient. A bottom sled portion of the shell serves to stabilize the positioning device under the mattress pad of the operating room table. This eliminates the need to provide a draw sheet to tuck the arms of the patient in place. Preferably, there is approximately a 2 inch elevation separating the hand shell and end cap from the sled base. This allows for the hand and arm of the patient to remain in alignment on top of the mattress covering the operating room table rather than off to the side of the table. The lower sled portion of the shell is recessed approximately 6 inches from the outer longitudinal end of the hand covering portion of the shell, so that the longitudinal length of the lower sled portion is approximately 6 inches less than the overall length of the outer hard shell of the positioning device, so as not to impose into the exposed operative work area as the moveable portion or leaf of the operating room table is lowered or removed. The hand covering or enclosing portion of the shell protects the fingers of the patient from becoming caught and injured during the replacement of the moveable portion of the operating room table into a normal coplanar position with respect to the remaining portion of the operating room table.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein:

FIG. 1 is a perspective view of an apparatus for positioning a portion of a body of a patient during surgery according to the present invention;

FIG. 2 is a side elevational view of the apparatus according to the present invention;

FIG. 3 is a side elevational view of disposable cushion means with contoured palm portion according to the present invention;

FIG. 4 is an exploded perspective view of an alternative configuration of the medical positioning apparatus according to the present invention;

FIG. 6 is a perspective view of an alternative reversible configuration of the medical positioning apparatus according to the present invention; and FIG. 7 is a detailed view of attachment means for a portion of the medical positioning apparatus according to the present invention with respect to a separable surgical sled.

DESCRIPTION OF THE PREFERRED AND ALTERNATIVE EMBODIMENTS

Figure 5:
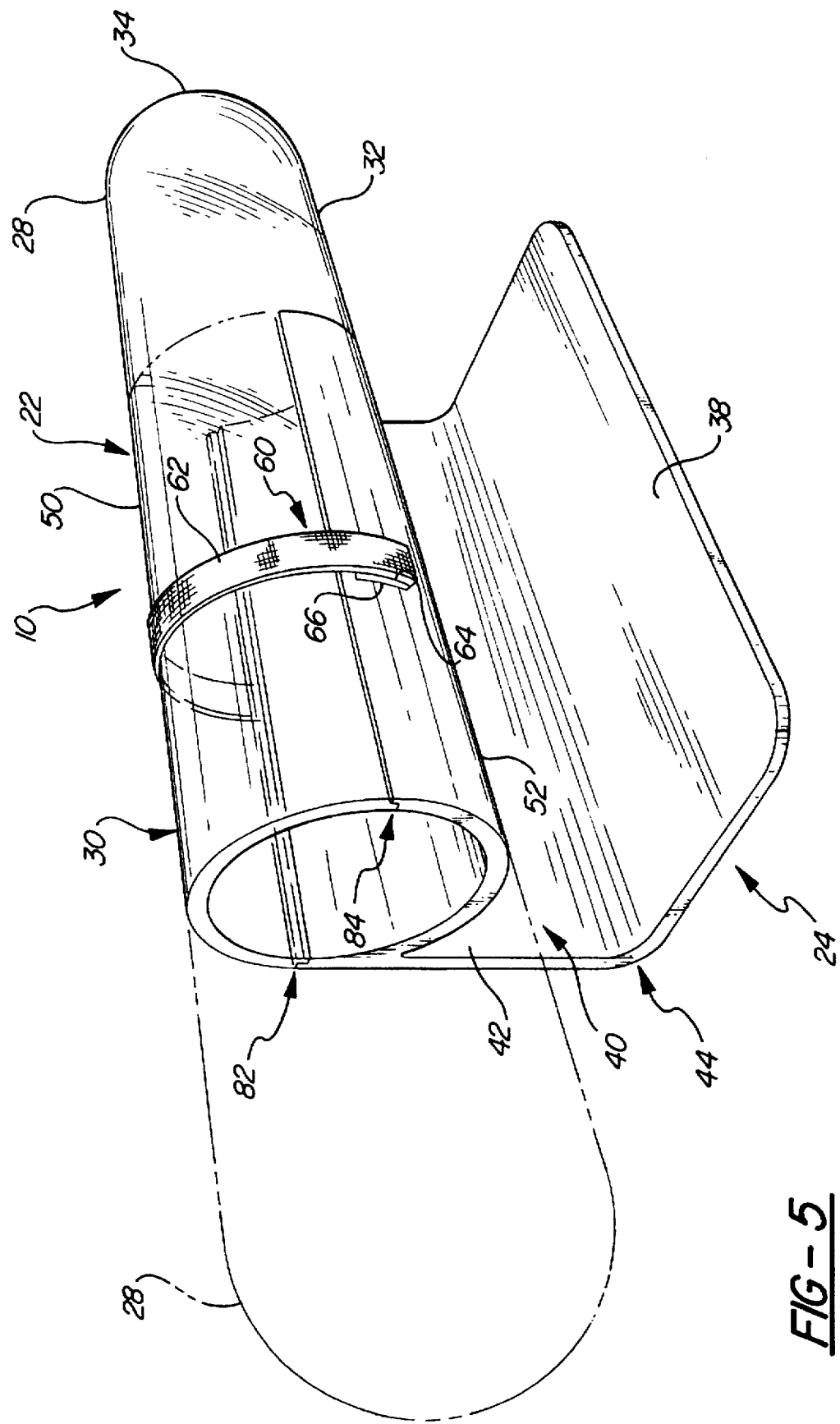
FIG. 5 is a perspective view of a reversible medical positioning apparatus according to the present invention allowing use for either a right-side appendage or a left-side appendage of a patient.

An apparatus 10 positions and protects an upper appendage portion 12 of a body of a patient with respect to an operating room table 14 having a mattress 16 covering at least a portion of the operating room table 14. A leaf portion 18 of the operating room table 14 is movable out of a coplanar position with respect to a remaining portion 20 of the table 14, such as during a surgical procedure.

An apparatus 10 according to the present invention can include means 22 for safeguarding or for preventing injury to an upper appendage 12 of the patient due to an object external to the body during a surgical procedure. Means 24 is also provided for anchoring the safeguarding or injury preventing means 22 in a desired location during the surgical procedure. The present invention may also include a disposable cushioning means 26 engagable about an arm of the patient from a first end above an elbow of the patient to a second end adjacent the fingers of the patient for protecting an ulnar nerve of the patient during the surgical procedure. Preferably, the disposable cushioning means 26 is at least partially receivable within the safeguarding or injury preventing means 22 during the surgical procedure.

The safeguarding or injury preventing means 22 can extend along a substantial portion of the upper appendage of the patient and can include a sleeve-like member 28 for fitting around at least a portion of the upper appendage 12 of the patient. The sleeve-like member 28 can include an elongated housing 30 for substantially enclosing a hand or at least fingers of the patient. The housing 30 can have a generally cylindrical side wall 32 with an end wall 34 closing one longitudinal end of the housing 30. The safeguarding or injury preventing means 22 is for restraining movement of the hand and/or fingers of the patient while unconscious during the surgical procedure. The safeguarding means 22 can include a hollow cylindrical sleeve member 28 with a permanent cylindrical side wall 32 for protecting fingers of the hand of the patient from injury during movement of the moveable leaf portion 18 of a surgical table 14 while the patient is unconscious during the surgical procedure. Preferably, the safeguarding or injuring preventing means 22 is elongated along a longitudinal axis and cantilevered passed an end edge 36 of a base portion 38 of the anchoring means 24, so that the hand and/or fingers of the patient is supported while the moveable leaf portion 18 of the surgical table 14 is lowered from beneath the hand. The safeguarding or injury preventing means 22 protects the hand and/or fingers from pinching injury when the movable portion 18 of the surgical table 14 is returned to a coplanar position with respect to the remaining portion 20 of the surgical table 14.

The anchoring means 24 according to the present invention can include a support member portion 40 connectible to or integrally formed with respect to the safeguarding means 22. The support member 40 can include a generally planar base portion 38 and an outwardly extending portion 42. The base portion 38 is positionable beneath a portion of a mattress 16 disposed on top of the operating room table 14, so that the safeguarding or injury preventing means 22 rests on top of the mattress 16, while the base portion 38 is anchored beneath the mattress 16. When in this position, the arm of the patient is supported on top of the mattress 16, while the weight of the patient maintains the apparatus 10 in the desired position with respect to the operating room table 14. In other words, the base portion 38 of the apparatus 10 is interposed between the mattress 16 and the operating room table 14 and is held in place by the weight of the patient.

As best seen in FIGS. 1 and 2, the safeguarding or injury preventing means 22 and anchoring means 24 are formed as an integral one piece apparatus 10 with an elongated rigid shell or housing 30. The housing 30 has a shallow curve for covering a lateral aspect of the arm of the patient and a sleeve-like member 28 having a cylindrical side wall 32 with an end cap or end wall 34 integrally formed to enclose one end of the shell 30 for completely covering at least the hand and fingers of the patient. A sled portion 44 is defined by the base portion 38 and support member portion 40 integrally formed as a portion of the shell 30 for stabilizing the shell 30 with respect to the operating room table 14. The base portion 38 of the sled 44 is spaced from the outer end of the end cap 34 along the longitudinal length of the shell 30 a sufficient distance to allow unimpeded movement of the leaf portion 18 of the operating room table 14 to and from a position coplanar with the remaining portion 20 of the operating room table 14. The sleeve-like member 28 can be formed with an open aperture or window 68 to allow access and inspection of the fingers of the patient as maybe required during the surgical procedure.

As best seen in FIGS. 2 and 3, the disposable cushioning means 26 can include a disposable liner 46 engagable about the arm of the patient from a first end above an elbow of the patient to a second end adjacent the fingers of the patient for protecting an ulnar nerve of the patient. The liner 46 is at least partially receivable within the injury preventing or safeguarding means 22 during a surgical procedure. The disposable liner 46 can be constructed of foam approximately one inch thick formed in a cylinder-like configuration, or rollable into a cylinder form. The liner 46 is engagable with an upper appendage portion of the patient between a first end positionable between a shoulder and an elbow of the patient, and a second end positionable adjacent fingers of a hand of the patient. Preferably, the cylindrical form of the liner 46 includes two open opposite ends to allow medical personnel to pull the arm of a patient through the foam cylinder, if the patient is unconscious. The liner 46 extends longitudinally along a length of the arm of the patient to protect the ulnar nerve of the patient and generally covers the elbow, wrist and hand of the patient. The liner 46 generally defines an open ended sleeve when sheathing the arm of the patient. Preferably, the liner 46 includes a contoured portion 48 conforming to a natural contour of the hand adjacent a palm of the hand of the patient for supporting the hand in a natural contour. The disposable liner 46 can be split into two parts along parting line 76 so that application of the disposable foam liner 46 is easier and at the user's discretion. In addition, it maybe desirable to use only the bottom half 78 of the disposable line 46 which cradles the underside of the arm and hand of the patient. The upper half 80 is optional under such circumstances. The lower portion of the sleeve-like member 28 as best seen in FIG. 1 is relatively flat along its bottom surface, or slightly less curved than the other portions of the sleeve-like member 28 along the length of the cap. Correspondingly, the lower portion 78 of the disposable liner 46 can include a flattened bottom portion, while maintaining a curved interior surface to cradle the arm and hand.

Referring now to FIG. 4, an alternative configuration of the elongated, rigid shell or housing 30 is illustrated. In this configuration, the sleeve-like member 28 extends along a longitudinal length of the housing 30 and is split into first and second housing portions, 50 and 52 respectively, moveable with respect to one another. The first and second housing portions, 50 and 52, have mating complementary surfaces, 54 and 56 respectively, engageable with one another along a parting line 58. Preferably, the complementary first and second surfaces, 54 and 56, are in the form of a tongue and groove configuration along the parting line 58. Means 60 is provided for connecting the first and second housing portion 50 and 52 with respect to one another in a sheathing relationship about an arm and hand of a patient during a surgical procedure. The connecting means 60 preferably includes at least one elongated strap 62 having a fastener 64 engagable with a complementary fastening portion or member 66. In the FIG. 4, by way of example and not limitation, the fastener 64 and complementary fastening member 66 are illustrated as hook and loop material, such as VELCRO. In this configuration, an optional aperture or window 68 can also be provided either a permanently open window 68 as illustrated in FIG. 1, or a window 68 having a sliding panel or other cover 70 to allow for easy access to the hand should it be necessary to access an intravenous (IV) connection to the patient without disturbing the position of the arm of the patient. Either an open window 68 or open window 68 having a slidable cover 70 can be incorporated into any of the embodiments disclosed in the present application as an optional configuration. The sliding cover 70 can be guided within opposing slots or tracks 72 and 74 respectively as illustrated in FIG. 4. The cover 70 can be moved between a first position opening the window 68 and a second position closing the window 68.

Referring now to FIG. 5, an alternative embodiment of the present invention is disclosed. In this embodiment, the first and second housing portion 50 and 52 respectively are slightly reconfigured to provide the upper and lower portions of the sleeve-like member 28 adjacent one end in a reversible form. The upper edge of the second housing portion 52 and the lower edge of the first housing portion 50 include complementary surfaces extending along the longitudinal edges 82 and 84. The safeguarding or injuring preventing means 22 and anchoring means 24 can be formed as separate pieces with respect to the elongated rigid shell or housing 30. The housing 30 has a shallow curve for covering a lateral aspect of the arm of the patient and a sleeve-like member 28 having a substantially cylindrical side wall 32 with an end cap or end wall 34 integrally formed to enclose an end of the shell 30 for completely coving at least the hand and fingers of the patient. The housing 30 and sleeve-like member 28 can be formed of plastic, metal or a clear acrylic material to allow inspection through the portion of the housing 30 coving the hand of the patient. In the alternative, the sleeve-like member 28 can include an aperture 68 as shown in FIG. 1 or an aperture and cover, 68 and 70 respectively, as illustrated in FIG. 4. A sled portion 44 is defined by the base portion 38 and support member portion 40 integrally formed as a portion of the lower part of the split housing 30. The housing 30 being split into first and second housing portion, 50 and 52 respectively, movable with respect to one another as previously described. The sled portion 44 stabilizes the shell 30 with respect to the operating room table 14. The base portion 38 of the sled 44 is spaced from the outer end of the end cap 34 along the longitudinal length of the shell 30 a sufficient distance to allow unimpeded movement of the leaf portion of the operating room table to and from a position coplanar with the remaining portion of the operating room table. Means 60 is provided for connecting the first and second housing portions 50 and 52 with respect to one another in a sheathing relationship about an arm and hand of the patient during a surgical procedure. Preferably, the complementary first and second surfaces along longitudinally extending edges 82 and 84 are in the form of a tongue and groove configuration allowing the upper portion 50 and the sleeve-like member 28 to be disposed in the first position illustrated in solid lines in FIG. 5 or the second position illustrated in phantom in FIG. 5 allowing the apparatus 10 according to the present invention to be used on either the right or left appendage of a patient without modification. The connecting means 60 can include at least one elongated strap 62 having a fastener 64 engageable with a complementary fastening portion or member 66. In FIG. 5, by way of example and not limitation, the fastener 64 and complementary fastening member 66 are illustrated as hook and loop material, such as VELCRO.

Referring now to FIGS. 6 and 7, an alternative embodiment of the apparatus 10 according to the present invention is illustrated. Means 22 is provided for safeguarding or preventing injury to an upper appendage of the patient by any object external to the body during a surgical procedure. Means 24 anchors the safeguarding or injuring preventing means 22 in a desired location during the surgical procedure. The safeguarding means 22 can extend along a substantial portion of the upper appendage of the patient. The anchoring means 24 can include a support member portion 40 connectable to or integrally formed with respect to the safeguarding means 22. The support member 40 can include a generally planar base portion 38 and an outwardly extending portion 42. The base portion 38 is positionable beneath a portion of a mattress disposed on top of the operating room table for anchoring the base portion 38 with respect to the patient. The safeguarding or injuring preventing means 22 can be formed of first and second separable portions. The first portion, such as elongated rigid shell or housing 30, can be formed as an integral, one piece member with anchoring means 24. The second portion, such as sleeve-like member 28 can be connected to either longitudinal end of the rigid shell or housing 30. The housing 30 has a shallow curve for covering a lateral aspect of the arm of the patient. Means for connecting the sleeve-like member 28 to the housing 30 is provided. The connecting means 86 can include one or more apertures 88 adjacent each longitudinal end of the housing 30. Each aperture 88 is adapted to receive a corresponding tab 90 formed adjacent an outer end of a finger 92 extending from the sleeve-like member 28. The material of the finger 92 is selected to include some flexibility and spring-back characteristics, so that the tab 90 can be slidably engaged within the aperture 88 of the housing 30 to releasably hold the sleeve-like member 28 with respect to the rigid housing 30. In addition, the tab 90 can be displaced for removal from the aperture 88 at on end of the housing 30 for placement at an opposite end of the housing 30 allowing the sleeve-like member 28 to be releasably engaged on either end of the elongated housing 30 as desired to protect either the right hand or left hand of a patient during the surgical procedure. Preferably, the sleeve-like member 28 is formed of a metal, plastic or clear acrylic material. The sleeve-like member 28 can be formed with an open aperture, or an aperture with a slidable cover as illustrated in FIGS. 1 or 4. Preferably, any embodiment of the present invention is used in combination with the disposable cushioning means 26 as illustrated in FIG. 3. The outer shell portion or sleeve-like member 28 of the present invention snaps on and off in an interchangeable, reversible manner with respect to the rigid housing portion 30 of the sled 34 to accommodate either the right or left appendage of a patient. One or more snap-on fasteners can be located on the longitudinal end of the sleeve-like member 28 with corresponding apertures formed in the longitudinal end of the rigid housing 30. The pressure wedge or tab 90 can be insert within the aperture or slot formed in the rigid housing 30 in order to lock the sleeve-like member 28 in place with respect to the rigid housing 30. It should be recognized that the snap-on tab 90 could be formed on the rigid housing 30 while the aperture is formed in the sleeve-like member 28 without departing from the spirit and scope of the present invention.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An apparatus for positioning a hand and arm of a patient with respect to a mattress disposed on top of a surgical table, said surgical table having a drop leaf portion moveable out of a coplanar position with respect to a remaining portion of the surgical table during a surgical procedure, said apparatus comprising:

an elongated sled for preventing injury to an upper appendage of the patient due to an object external to the body during the surgical procedure, said sled having a first portion positionable below said mattress and a second portion extending outwardly from said first portion to a position above said mattress partially sheathing said arm of said patient; and an end cap releasibly engageable with either longitudinal end of said sled and positionable on top of said mattress for releasibly sheathing said hand of said patient, said end cap spaced vertically above said first portion of said sled allowing insertion of said mattress therebetween.

2. The apparatus of claim 1 further comprising:

said end cap including a hand sheathing portion for preventing pinching injury to the hand of the patient when the drop leaf portion of the surgical table is returned to the coplanar position with respect to the remaining portion of the surgical table during a surgical procedure while the patient is unconscious, said hand sheathing portion extending beyond an edge of the remaining portion of the surgical table defined by a joint connecting the drop leaf portion to the remaining portion of the surgical table.

3. The apparatus of claim 1 further comprising:

a separate, disposable liner independent of said sled and end cap, said liner engageable about an arm of the patient prior to insertion within said sled and end cap, said liner extendible from a first end above an elbow of the patient to a second end adjacent the fingers of the patient for protecting an ulnar nerve of the patient, the liner at least partially receivable within the sled and end cap during a surgical procedure.

4. The apparatus of claim 1 further comprising:

said end cap including a hollow cylindrical sleeve member split into first and second housing portions moveable with respect to one another, the first and second housing portions having mating complementary surfaces along a parting line; and means for connecting the first and second housing portions with respect to one another to sheath an arm and a hand of a patient during a surgical procedure.

5. The apparatus of claim 1 wherein the sled further comprises:

a support member connectible with respect to the end cap, the support member defined by said first portion, said first portion including a generally planar base and said second portion including an outwardly extending member projecting from the base, the base releasably positionable beneath a portion of said mattress disposed on top of the surgical table so that the end cap rests on top of the mattress while the base is anchored beneath the mattress.

6. The apparatus of claim 5 further comprising:

said end cap having a longitudinal axis and cantilevered passed an end edge of the base of the sled so that a hand of the patient is supported while a moveable portion of the surgical table is lowered from beneath the hand, the end cap for protecting the hand from pinching injury when the moveable portion of the surgical table is returned to a coplanar position with respect to the surgical table.

7. An apparatus for positioning an arm and hand of a patient with respect to an operating room table having a mattress covering at least a portion of the operating room table and a leaf portion moveable out of a coplanar position with respect to a remaining portion of the operating room table during a surgical procedure, the apparatus comprising:

a separate, independent, disposable cushion engageable with the arm and hand of the patient prior to placing the patient on the operating room table, said cushion extendible between a first end positionable between a shoulder and an elbow of the patient and a second end positionable adjacent fingers of the hand of the patient, the cushion extending longitudinally along a length of the arm of the patient to protect an ulnar nerve area of the patient and generally covering the elbow, wrist and hand of the patient, the cushion generally defining an open ended sleeve when sheathing the arm of the patient, the cushion including a contoured portion adjacent a palm of the hand of the patient for supporting a natural contour of the hand; and an elongated rigid shell having a shallow curve for covering a lateral aspect of the arm of the patient and an end cap integrally formed to enclose one end of the shell for completely covering at least the hand and fingers of the patient, a sled integrally formed as a portion of the shell for stabilizing the shell with respect to the operating room table, a base portion of the sled is spaced from the end cap a sufficient distance to allow insertion of the mattress covering the operating room table between the end cap and the base portion of the sled, the base portion of the sled is spaced longitudinally inwardly from an outer end of the end cap along the longitudinal length of the shell a sufficient distance to allow unimpeded movement of the leaf portion of the operating room table to and from a position coplanar with the remaining portion of the operating room table.

8. In an apparatus for protecting a patient's hand and arm from injury while the patient is lying on a treatment table, the improvement comprising:

a unitary, one-piece sled for placement at least partially under a mattress covering said treatment table, the sled having a base portion positionable under said mattress and a shell portion extending from the base portion above the mattress for protecting the patient's arm;

an end cap housing spaced above the base portion and positionable on top of the mattress for protecting the patient's hand, said end cap housing supportable from the shell portion of the sled; and window means extending through a surface of said end cap housing for allowing inspection of a patient's hand during surgery.

9. The improvement of claim 8 further comprising:

said end cap housing integrally formed as part of said unitary, one piece sled.

10. The improvement of claim 8 further comprising:

said window means including an aperture extending through the end cap housing.

11. The improvement of claim 10 further comprising:

cover means for selectively opening and closing said aperture permitting access to said patient's hand within said end cap housing.

12. In an apparatus for protecting a patient's hand and arm from injury while the patient is lying on a treatment table, the improvement comprising:

a unitary, one-piece sled for placement at least partially under a mattress covering said treatment table, the sled having a base portion positionable under said mattress and a shell portion extending from the base portion above the mattress for protecting the patient's arm;

an end cap housing spaced above the base portion and positionable on top of the mattress for protecting the patient's hand, said end cap housing supportable from the shell portion of the sled; and releasible means for selectively connecting the end cap housing to either longitudinal end of the shell portion of the sled, thereby allowing the sled and end cap housing to be used selectively on the right side and the left side of the patient to protect the corresponding hand and arm.

13. The improvement of claim 12 further comprising:

said releasible means including at least one resilient outwardly extending finger supporting a tab on an outer end thereof with respect to one of said end cap housing and said shell portion of said sled, the other of said end cap housing and said sled having at least one complementary aperture for releasibly receiving said tab for holding said end cap housing in stationary position with respect to said sled after engagement therein.

14. In an apparatus for protecting a patient's hand and arm from injury while the patient is lying on a treatment table, the improvement comprising:

a unitary, one-piece sled for placement at least partially under a mattress covering said treatment table, the sled having a base portion positionable under said mattress and a shell portion extending from the base portion above the mattress for protecting the patient's arm;

an end cap housing spaced above the base portion and positionable on top of the mattress for protecting the patient's hand, said end cap housing supportable from the shell portion of the sled;

a separate, disposable cushion engageable with respect to said patient's arm prior to placement within said shell portion and end cap for protecting an ulnar nerve of the patient during surgery, said cushion at least partially positionable within said end cap housing, said cushion generally defining an open ended sleeve when sheathing the arm of the patient prior to insertion within the end cap housing of the sled.

15. The improvement of claim 14 further comprising:

said cushion having a contoured portion adjacent a palm of the hand of the patient for supporting a natural contour of the hand.

16. The apparatus of claim 14 further comprising:

said disposable cushion engageable about an arm of the patient from a first end above an elbow of the patient to a second end adjacent the fingers of the patient.

17. In an apparatus for protecting a patient's hand and arm from injury while the patient is lying on a treatment table, the improvement comprising:

a unitary, one-piece sled for placement at least partially under a mattress covering said treatment table, the sled having a base portion positionable under said mattress and a shell portion extending from the base portion above the mattress for protecting the patient's arm;

an end cap housing spaced above the base portion and positionable on top of the mattress for protecting the patient's hand, said end cap housing supportable from the shell portion of the sled, said end cap housing split into first and second housing portions moveable with respect to one another; and means for connecting the first and second housing portions with respect to one another to sheath an arm and a hand of the patient during a surgical procedure.

18. The improvement of claim 17 further comprising:

said first and second housing portions having mating complementary surfaces along a parting line.

* * * * *